US00PP09021P

United States Patent [19]

Olesen et al.

[11] Patent Number: Plant 9,021

[45] Date of Patent: Dec. 27, 1994

[54] MINIATURE ROSE PLANT NAMED POULTRE

[75] Inventors: Morgens N. Olesen; Pernille Olesen, both of Fredensborg, Denmark

[73] Assignee: Bear Creek Gardens, Inc., Medford, Oreg.

[21] Appl. No.: 209,845

[22] Filed: Mar. 11, 1994

[51] Int. Cl.[5] ..... A01H 5/00

[52] U.S. Cl. ..... Plt./9

[58] Field of Search ..... Plt. 9, 7.1

*Primary Examiner*—Howard J. Locker

*Attorney, Agent, or Firm*—Klarquist Sparkman Campbell Leigh & Whinston

[57] ABSTRACT

A miniature rose plant having attractive, light pink flowers; compact growth habit; ease of production from softwood cuttings; excellent keeping ability, and the production of many of the flowers in clusters.

1 Drawing Sheet

The present invention relates to a new and distinct variety of rose plant of the miniature class which was originated by us by crossing two unnamed seedlings.

The primary objective of this breeding was to produce a new rose variety having a low, compact growth habit suitable to grow from cuttings in a 6 cm pot; an attractive, light pink flower color; good keeping quality as a pot rose; and flower production in clusters. The objective was substantially achieved, along with other desirable improvements, as evidenced by the following unique combination of characteristics that are outstanding in the new variety and that distinguish it from its parents, as well as from all other varities of which we are aware:

1. Soft, light pink flower color;
2. Ease of production from softwood cuttings;
3. Excellent keeping quality;
4. Production of flowers in clusters; and
5. Compact growth habit.

Asexual reproduction of this new variety by softwood cuttings are performed at Wasco and Somis, Calif., and Fredensborg, Denmark, shows that the foregoing characteristics adn distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of our new rose cultivar with color descriptions using terminology in accordance with The Royal Horticultural Society (London) Colour Chart, except where ordinary dictionary signficance of color is indicated.

Parentage:

*Seed parent.*—Unnamed seedling.

*Pollen parent.*—Unnamed seedling.

Classification:

*Botanical.*—*Rosa hybrida.*

*Commercial.*—Miniature.

FLOWER

Observations made from specimens grown in greenhouse environments as Somis, Calif., and Fredensborg, Denmark.

Blooming habit: Recurrent.

Bud:

*Size.*—13 mm long when the petals start to unfurl.

*Form.*—The bud form is short, pointed ovoid.

*Color.*—When sepals first divide, bub color is Red Group 49C. When half brown, the upper and lower sides of the petals are Red Group 49C.

*Sepals.*—Color: Green Group 138C. Surface texture: Covered in fine hairs. There are three normally appendaged sepals. There are tw3o unappendaged sepals with hairy edges.

*Receptacle.*—Color: Green Group 141C. Shape: Funnel. Size: Small (3 mm by 3 mm). Surface: Smooth.

*Peduncle.*—Length: Short (2.5 cm). Surface: Smooth. Color: Light green. Strength: Stiff, erect.

Bloom:

*Size.*—Small. Average open size is about 6 cm.

*Borne.*—Singly, several together, in pyramidal clusters of 3 to 5 flowers.

*Stems.*—Short (12 to 15 cm); strong.

*Form.*—When first open: High centered. Permanence: Flattens, all petals curl, quill fashion.

*Petalage.*—Number of petals under normal conditions: 30 to 40.

*Color.*—The upper and reverse sides of the petals are Red Group 49C. The base of each petal has a Yellow Group 2C half-moon at the point of attachment. The major color on the upper side is Red Group 49C.

*Variegations.*—None.

*Discoloration.*—The general tonality at the end of the first day: No change. At the end of the third day, no change. By day 7 or 8 there is a gradual fading to Red Group 49D.

*Fragrance.*—Slight.

Petals:

*Texture.*—Thin.

*Shape.*—Deltoid.

*Form.*—Tips slightly recurved, edges slightly quilled.

*Arrangement.*—Imbricated, with few petaloids in the center.

*Persistence.*—Drop off cleanly.

*Lastingness.*—On the plant: Very long (14 to 16 days). As a cut flower: Very long (10 to 12 days).

Reproductive Parts:

*Anthers.*—Size: Small. Quantity: Many. Color: Yellow. Arrangement: Regular around styles.

*Filaments.*—Color: White.

*Pollen.*—Color: Lemon yellow.

*Styles.*—Color: White with some pink.

*Stigmas.*—Color: Greenish white.

Form: Bush.

Growth: Vigorous, dwarf, upright, branching. Plant is 30 to 36 cm tall and 25 cm wide.

Foliage: Number of leaflets on normal mid-stem leaves: 5.

*Size.*—Small (6 cm×4 cm).

*Quantity.*—Normal.

*Color.*—New foliage: Green Group 137D. Old foliage: Green Group 137A.

Leaflets:

*Shape.*—Pointed oval.

*Texture.*—Upper side: Smooth.

*Edge.*—Serrated.

*Serration.*—Single, small.

*Petiole rachis.*—Color: Green.

*Petiole underside.*—Smooth, with occasional prickles.

*Stipules.*—Short, bearded.

*Disease resistance.*—Resistant to mildew and rust under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Few. On laterals from main canes: Few.

*form.*—Hooked slightly downward.

*Color when young.*—Green and red.

Small prickles:

*Quantity.*—On main stalks: None. On laterals: None.

We claim:

1. A new and distinct variety of rose plant of the miniature class, substantially as herein shown and described, characterized particularly as to novelty by the unique combination of its attractive, light pink flowers; compact growth habit; ease of production from softwood cuttings; excellent keeping ability, and the production of many of the flowers in clusters.

* * * * *

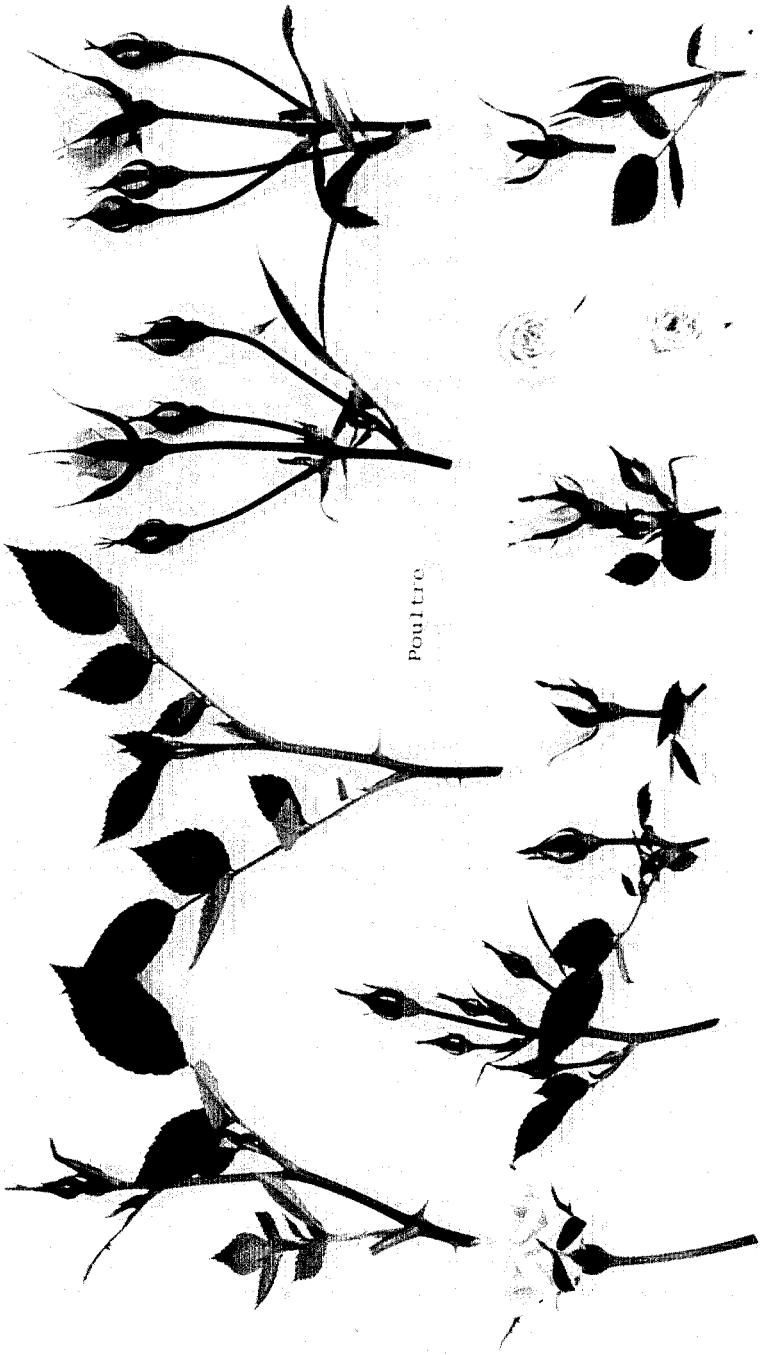
Poultre